United States Patent [19]

Kaufhold et al.

[11] Patent Number: 5,412,146
[45] Date of Patent: May 2, 1995

[54] PROCESS FOR THE PREPARATION OF 2-CYANOACETOXYPROPIONIC ESTERS

[75] Inventors: Manfred Kaufhold, Marl; Marcel Feld, Köln, both of Germany

[73] Assignee: Huels Aktiengesellschaft, Marl, Germany

[21] Appl. No.: 253,347

[22] Filed: Jun. 3, 1994

[30] Foreign Application Priority Data

Jun. 3, 1993 [DE] Germany .................. 43 18 381.6

[51] Int. Cl.$^6$ ............................................ C07C 253/30
[52] U.S. Cl. .................................... 558/442; 558/441
[58] Field of Search ............................. 558/441, 442

[56] References Cited

U.S. PATENT DOCUMENTS 4,582,648  4/1986  Hirakawa ........................... 558/442

FOREIGN PATENT DOCUMENTS 0127855  12/1984  European Pat. Off. .
0222461  12/1984  Japan ................................. 558/442

OTHER PUBLICATIONS

Chemical Abstracts, vol. 102, No. 24, Jun. 17, 1985, p. 10, 102: 204452h; Alpha Techno Co.

*Primary Examiner*—Joseph Paul Brust
*Attorney, Agent, or Firm*—Oblon, Spivak, McClelland, Maier & Neustadt

[57] ABSTRACT

For the preparation of 2-cyanoacetoxypropionic esters, a mixture of lactic ester and cyanoacetic ester is introduced, an alkali metal alcoholate is added as catalyst and the mixture is heated while the alcohol eliminated during the course of the reaction is distilled off. The course of the reaction is followed by means of gas chromatographic analysis and the reaction is terminated prior to eliminating the theoretical amount of alcohol by destroying the catalyst by acidification. The reaction mixture is worked up by distillation and the product easily separated from the reaction mass due to the substantial absence of high boiling components.

14 Claims, No Drawings

PROCESS FOR THE PREPARATION OF 2-CYANOACETOXYPROPIONIC ESTERS

BACKGROUND OF THE INVENTION

1. Field of the Invention

The invention pertains to a process for the preparation of 2-cyanoacetoxypropionic esters of the general formula III, in particular those having high optical purity, by reacting cyanoacetic esters I with lactic esters, in particular optically active lactic esters II, in the presence of a catalyst, with elimination of the alcohol radical from the cyanoacetic ester.

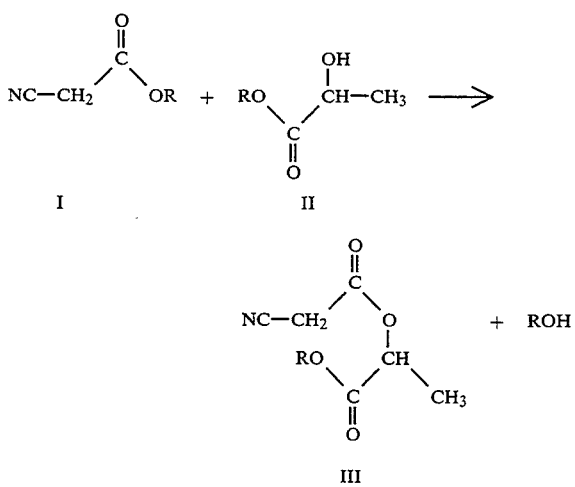

2. Description of the Related Art

Various processes are known from the literature for the preparation of III. Thus, EP-A 127,855 suggests, as a synthesis for III, the condensation of cyanoacetic acid with lactic esters with dehydration. Which chemical substances are required for this reaction, however, are not disclosed. In any case, expensive reagents are necessitated due to the fact that the dehydration must take place under gentle conditions, since otherwise high-boiling compounds are formed as the major product. This latter process is therefore relatively complex and uneconomical. A further problem is the thermal sensitivity of cyanoacetic acid. At slightly elevated temperatures, even below 100° C., it begins to decompose and at still higher temperatures, this decomposition can take place explosively. Thus, safety problems are also a major disadvantage of this process.

Japanese Patent JP 84/222,461 discloses a somewhat similar process starting with cyanoacetic acid and reacting this with an α-chlorinated ester. In order to prepare 2-cyanoacetoxypropionic esters, the latter process would require the use of an α-chloropropionic ester:

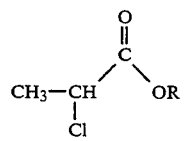

However, such α-chloropropionic esters are likewise unstable under the reaction conditions, so that in this synthesis pathway, both starting materials are unstable.

Commercialization is highly problematic given such conditions which, in summary, require expensive chemicals, deliver unsatisfactory yields and, moreover, also exhibit safety problems. A simple process is therefore desirable in which stable, easily accessible starting materials are used, for example esters, and in which these starting materials are reacted in the presence of a suitable catalyst without the use of additional reagents to give the target product.

The 2-cyanoacetoxypropionic ester products are important raw materials in the adhesives sector (see, for example EP-A 0,127,855) and in the pharmaceuticals field. Furthermore, for use as starting materials for pharmaceutical products, high optical purity is desirable, i.e., the optical activity which is introduced into the system by the use of optically active lactic esters must be maintained.

OBJECTS OF THE INVENTION

There is great interest in a process in which with little capital investment, the cost-effective and safe preparation of 2-cyanoacetoxypropionic esters may be achieved. These and other objects have been accomplished by the subject invention, wherein the esters of cyanoacetic acid and lactic acid are reacted in the presence of a catalyst with elimination of an alcohol, and the target product, the 2-cyanoacetoxypropionic ester, is isolated by simple distillation.

SUMMARY OF THE INVENTION

The invention pertains to a process for the preparation of 2-cyanoacetoxypropionic esters of the general formula:

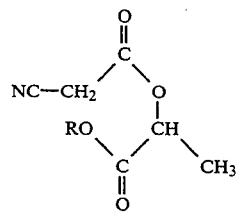

which is characterized in that cyanoacetic esters of the general formula I are reacted with lactic esters of the general formula II

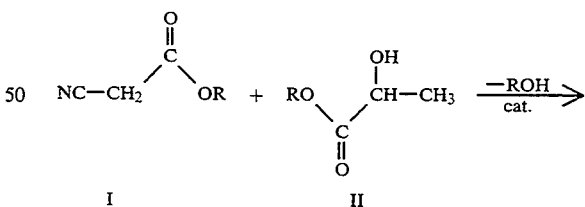

in which R denotes a $C_1$–$C_{10}$-hydrocarbon radical, in the presence of a basic catalyst, distilling off the corresponding eliminated alcohol, and terminating the reaction prior to realizing the theoretically possible amount of alcohol.

Surprisingly, pure 2-cyanoacetoxypropionic esters are obtained if a cyanoacetic ester is reacted with a lactic ester in the presence of a metal alcoholate as catalyst, the corresponding alcohol being eliminated from the cyanoacetic ester. An important characteristic of the present invention is that this reaction is not carried out to completion, i.e., until the theoretically possible amount of alcohol is formed, but instead is terminated prior to completion, by destroying and inactivating the catalyst, e.g. by acidification.

If the reaction is not terminated, high-boilers, presumably polyesters, are formed which make isolation of the target products impossible or at least uneconomical. The course of the reaction can easily be followed by gas chromatographic analyses. It is then observed that from a content of, e.g., 50–60% of 2-cyanoacetoxypropionic esters, high-boilers are increasingly formed. This is then the correct point to terminate the reaction. It is highly surprising that the reaction of the two esters actually has such a high selectivity for the monomeric target product. Because of the diverse reaction possibilities, it would rather be assumed that valueless polyesters form directly, e.g. by lactic ester molecules themselves reacting together. This result could not have been predicted. The advantages of the process are its simple practice and its high efficiency.

DESCRIPTION OF THE PREFERRED EMBODIMENTS

The practical implementation of the reaction and the work-up are carried out, for example, in the manner expressed below.

A stirred apparatus having a distillation column and a vertical recovery bend is used. The two esters are introduced following which the catalyst is added with stirring. It is advantageous, especially in the case of relatively large industrial amounts and especially in the case of a continuous procedure, to first introduce the cyanoacetic ester, to add the catalyst, and then to meter in the lactic ester. The molar ratio of lactic ester to cyanoacetic ester is 1:1 to 1:20, preferably 1:1 to 1:10, in particular, 1:1.1 to 1:2, i.e., cyanoacetic ester is preferably used in excess. The molar ratio of catalyst to lactic, ester is 0.001:1 to 0.1:1, preferably 0.005:1 to 0.05:1, in particular 0.01:1 to 0.05:1.

The catalysts used are basic compounds, such as metal alcoholates, preferably those of the alkali metals and alkaline earth metals, such as Na, K, Mg, Ca, Sr, Ba, and straight-chain and/or branched $C_1$- to $C10$-alkanols. For economic reasons, particularly sodium methylate, ethylate or butylate or potassium methylate, ethylate or butylate are used. However, compounds can be alternatively used which form alcoholates or initially react with the hydroxyl group of the lactic ester, such as sodium hydride, sodium amide, Grignard compounds, and the like. After the components have been mixed, the mixture is heated and the alcohol formed is distilled off. The reaction temperature is then gradually increased so that distillate is continuously produced.

The reaction proceeds at 100° to 230° C. preferably at 120° to 200° C., in particular at 140° to 200° C. During the distillation, samples are continuously taken from the reactor and rapidly analyzed by gas chromatography, e.g. after 6, 8, 10 and 12 hours. When the analyses show that the content of the 2-cyanoacetoxypropionic ester is no longer increasing, but in contrast, that of the high-boilers is increasing, the reaction is terminated. The reaction time can also first be determined in a preliminary trial, in order to have more reliability and to be able to plan better in production.

After the mixture is cooled it is acidified, e.g. using phosphoric acid, sulfuric acid, hydrochloric acid, nitric acid, other mineral acid, or an organic carboxylic acid such as formic acid, acetic acid etc., following which the batch is worked up by distillation. It is advantageous in this case, but not absolutely necessary, first to separate the desired reaction products and the unreacted starting materials from the high-boiling residue, and to use for this a high-boiling solvent which makes the residue more fluid. Solvents which are suitable are a multiplicity of chemical substances which have a high enough boiling point and are stable under the conditions, such as e.g. white oils, paraffins, alkylated aromatic compounds and the like. Thermal transfer fluids such as MARLOTHERM S and the like have proven to be economical. The distillate freed from residue is then purified by fractional distillation.

The 2-cyanoacetoxypropionic esters may be used for the preparation of adhesives (see above-mentioned EP). In addition, these esters are important intermediates for the preparation of pharmaceutical products.

Having generally described this invention, a further understanding can be obtained by reference to certain specific examples which are provided herein for purposes of illustration only and are not intended to be limiting unless otherwise specified.

EXAMPLE 1

A glass apparatus is used which is composed of a three-necked flask, a stirrer, thermometer, distillation column and vertical recovery bend with a receiver. The following are used:

509 g (5.14 mol) of methyl cyanoacetate 437 g (4.2 mol) of methyl L(-)lactate 14 g of sodium methylate, dissolved in methanol (30 %)

The products are introduced, mixed and heated. From approximately 140° C., particularly from 150° C., methanol is produced which is distilled off. In order that distillate be continuously produced, the reaction temperature is gradually increased, up to approximately 200° C. Samples are taken from the reactor after 6, 8, 10 and 12 hours and are analyzed. The GC analyses show the following course of reaction:
(Abbreviations:
Methyl lactate (ML)
Methyl cyanoacetate (MCA)
Methyl-2-cyanoacetoxypropionate (MCAP)
Unknown high boiling components (UHC)

| Sample No. | ML | MCA | MCAP | UHC |
|---|---|---|---|---|
| 1 (after 6 h) | 30 | 44 | 25 | 0.2 |
| 2 (after 8 h) | 24 | 39 | 36 | 0.4 |
| 3 (after 10 h) | 16 | 31 | 51 | 0.7 |
| 4 (after 12 h) | 11 | 27 | 57 | 0.9 |

After the reaction time of 12 hours, the reaction is terminated by cooling and acidifying with 6.0 g of phosphoric acid (85% strength). The methanol production is 140 g.

In order to be able to separate material more easily from the high-boiling residue, 300 g of MARLOTHERM S were added to the reaction product and the product is taken off on a vertical recovery bend in vacuo at 0.2 mbar and a temperature range from 42° to 164° C. A total of 666 g of distillate is obtained which contains MCAP in a concentration of approximately 57%. By fractional distillation, MCAP in 96% purity is obtained at 13 mbar over a temperature range from 153° to 155° C. The conversion rate of lactic ester is 79% and the yield of distilled MCAP, based on unreacted ester, is 62% of theory. The optical rotation is −54°.

COMPARATIVE EXAMPLE

The apparatus and starting materials employed in Example 1 are used. The procedure is carried out as described in Example 1, with the difference that the reaction is not terminated, e.g. after 12 hours, but is allowed to proceed to completion as is otherwise conventional, that is to say for 17 hours. The following are the results obtained:

| GC analyses of the reaction course samples | | | | |
|---|---|---|---|---|
| Sample No. | ML | MCA | MCAP | UHC |
| 1 (after 6 h) | 30 | 42 | 25 | 0.2 |
| 2 (after 7.5 h) | 23 | 37 | 37 | 0.4 |
| 3 (after 10 h) | 17 | 31 | 49 | 0.7 |
| 4 (after 12 h) | 11 | 25 | 59 | 0.9 |
| 5 (after 14 h) | 10 | 20 | 59 | 1.4 |
| 6 (after 16 h) | 12 | 18 | 53 | 3.0 |
| 7 (after 17 h) | 13 | 17 | 50 | 4.0 |

The reaction product is composed of a highly viscous, sticky, dark brown intractable mass which cannot be worked up by conventional methods. In comparison to Example 1, it can be seen that the reaction must be terminated much earlier.

EXAMPLE 1 and 3

The apparatus and starting materials employed in Example 1 are used, with the difference that the initial quantity of methyl cyanoacetate is decreased in one case to a molar ratio of the esters of 1:1 and in the other case is increased to a molar ratio of 1:10. In the first case, a yield of MCAP of 45% of theory is achieved, and in the second case 72% of theory based on unreacted lactic ester. The conversion rates are 76 and 81% respectively.

EXAMPLE 4 and 5

The apparatus and starting materials employed in Example 1 are used, but with the difference that the initial quantity of catalyst is decreased in one case to a molar ratio of sodium methylate to lactic ester of 0.01:1 and in the other case is increased to a solar ratio of 0.05:1.

The favorable time points for terminating the reaction are again determined by gas chromatographic analysis. In the first case, the reaction is terminated after 15 hours. The conversion rate of lactic ester is 85% and the yield of distilled MCAP, based on unreacted ester, is 48% of theory. In the second case, the reaction is terminated after 10 hours. The conversion rate of lactic ester is 83% and the yield of distilled MCAP, based on unreacted ester, is 53% of theory. The examples therefore show that the most favorable time point for terminating the reaction must be determined individually when the reaction conditions are changed.

EXAMPLE 6

Apparatus, procedure, and starting materials are as in Example 1, with the difference that potassium methylate is used instead of sodium methylate. The reaction is terminated after 11 hours. The remaining results are comparable with those of Example 1.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A process for the preparation of 2-cyanoacetoxy-propionic esters of the general formula III:

$$NC-CH_2-CO-O-CH(CH_3)-CO-OR \quad (III)$$

comprising mixing cyanoacetic esters of the general formula I with lactic acid esters of the general formula II:

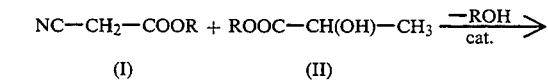

$$(I) \quad\quad (II)$$

wherein R denotes a $C_1$-$C_{10}$ hydrocarbon radical in the presence of a basic catalyst; heating the resulting mixture to promote the reaction of I with II to form III with elimination of an alcohol, ROH; distilling off the alcohol; and terminating the reaction before obtaining the theoretically possible amount of alcohol and after having obtained, in a product mixture containing I, II, III, and any unknown high boiling components (UHC), at least about 25% III of the total amount of I, II, III, and any UHC.

2. The process of claim 1, wherein the reaction temperature is from 100° C. to 230° C.

3. The process of claim 1, wherein the molar ratio of cyanoacetic ester to lactic ester is from 20:1 to about 1:1.

4. The process of claim 1, wherein the molar ratio of cyanoacetic ester to lactic ester is from 10:1 to about 1:1.

5. The process of claim 1, wherein the molar ratio of cyanoacetic ester to lactic ester is from 2:1 to about 1.1:1.

6. The process of claim 1, wherein said catalyst is an alkaline earth alcoholate or alkali metal alcoholate.

7. The process of claim 6, wherein said metal of said metal alcoholate is selected from the group consisting of Na, K, Mg, Sr, Ba, and mixtures thereof, and said alcoholate is derived from a $C_1$-$C_{10}$ straight or branched chain alkanol.

8. The process of claim 1, wherein said catalyst is present in an amount of from 0.001 to 0.01 mole per mole of lactic ester.

9. The process of claim 8, wherein said catalyst is present in an amount of from 0.0005 to 0.5 mole per mole of lactic ester.

10. The process of claim 8, wherein said catalyst is present in an amount of from 0.01 to 0.5 mole of lactic ester.

11. The process of claim 1, wherein the reaction temperature is from 140° C. to 200° C.

12. The process of claim 11, wherein the molar ratio of cyanoacetic ester to lactic ester is from 20:1 to about 1:1.

13. The process of claim 1, wherein said catalyst is present in an amount of from 0.005 to about 0.05 mole per mole of lactic ester; said reacting takes place at a temperature of from 140° C. to 200° C.; wherein said catalyst is selected from the group consisting of sodium methylate, sodium ethylate, sodium butylate, potassium methylate, potassium ethylate, potassium butylate, and mixtures thereof; and wherein the molar ratio of cyanoacetic ester to lactic ester is from 10:1 to 1:1.

14. The process of claim 13, wherein said catalyst is present in an amount of from 0.01 to about 0.05; and wherein said molar ratio of cyanoacetic ester to lactic ester is from 2:1 to 1.1:1.

* * * * *